(12) United States Patent
Puskas et al.

(10) Patent No.: US 8,871,937 B2
(45) Date of Patent: Oct. 28, 2014

(54) 8-HYDROXY-QUINOLINE DERIVATIVES

(75) Inventors: Laszlo Puskas, Szeged (HU); Csaba Szabo, Gyor (HU); Ivan Kanizsai, Szeged (HU); Mario Gyuris, Szeged (HU); Ramona Madacsi, Pirto (HU); Bela Ozsvari, Szeged (HU); Liliana Feher, Szeged (HU); Gabor Tamas, Szeged (HU)

(73) Assignees: "AVIDIN" Kutato, Fejleszto es Kereskedelmi Korlatolt Felelossegu Tarsasag, Szeged (HU); UBICHEM Kutato Korlatolt Felelossegu Tarsasag, Budapest (HU)

( * ) Notice: Subject to any disclaimer, the term of this patent is extended or adjusted under 35 U.S.C. 154(b) by 0 days.

(21) Appl. No.: 13/696,541

(22) PCT Filed: May 6, 2011

(86) PCT No.: PCT/HU2011/000043
§ 371 (c)(1),
(2), (4) Date: Jan. 14, 2013

(87) PCT Pub. No.: WO2011/148208
PCT Pub. Date: Dec. 1, 2011

(65) Prior Publication Data
US 2013/0131096 A1 May 23, 2013

(30) Foreign Application Priority Data

May 6, 2010 (HU) ..................................... 1000243

(51) Int. Cl.
| C07D 215/38 | (2006.01) |
| C07D 401/10 | (2006.01) |
| C07D 401/06 | (2006.01) |
| C07D 401/14 | (2006.01) |
| C07D 413/12 | (2006.01) |
| C07D 401/12 | (2006.01) |
| C07D 215/26 | (2006.01) |

(52) U.S. Cl.
CPC ............ *C07D 413/12* (2013.01); *C07D 401/10* (2013.01); *C07D 401/06* (2013.01); *C07D 401/14* (2013.01); *C07D 401/12* (2013.01); *C07D 215/26* (2013.01)
USPC ........................................................ 546/159

(58) Field of Classification Search
USPC ........................................................ 546/159
See application file for complete search history.

(56) References Cited

U.S. PATENT DOCUMENTS

| 8,618,302 B2 * | 12/2013 | Errico et al. ................... 546/175 |
| 8,658,170 B2 * | 2/2014 | Errico et al. ................ 424/133.1 |
| 2009/0088420 A1 * | 4/2009 | Neamati et al. .......... 514/217.07 |

FOREIGN PATENT DOCUMENTS

| WO | 2008/116092 | * | 9/2008 |
| WO | 2009/051801 | * | 4/2009 |

OTHER PUBLICATIONS

Smirnova, Chem & Bio, vol. 17, pp. 380-391, Apr. 2010.*
McLean, Bioorg Med Chem Lett, vol. 19, pp. 6717-6720, 2009.*
Brozic, Mol & Cell Encocrinology, vol. 301, pp. 245-250, 2009.*

* cited by examiner

*Primary Examiner* — D Margaret M Seaman
(74) *Attorney, Agent, or Firm* — Olson & Cepuritis, Ltd.

(57) ABSTRACT

The invention relates to compounds of the general formula (I) and their pharmaceutically acceptable salts (in which formula $R_1$ represents a hydrogen atom, lower alkyl group, lower alkenyl group, lower cycloalkyl group, aryl group, aralkyl group or heterocyclic group, wherein, the above groups are optionally substituted in ortho, meta and/or para position with 1, 2, 3 or 4 electron withdrawing groups or electron donating groups;

$R_2$ represents a hydrogen atom, lower alkyl group, aryl group, aralkyl group or heterocyclic group wherein the above groups are optionally substituted with one or more halogen atoms;

$R_3$ represents a lower alkyl group, aryl group, aralkyl group or heterocyclic group wherein the above groups are optionally substituted in ortho, meta or para position with 1, 2, 3 or 4 electron withdrawing groups or electron donating groups; $R_4$ represents a hydrogen atom, lower alkyl group or any acidic functional group;

n is 1 or 2).

The compounds according to the invention can be used in the medicine mainly for the treatment of diseases associated with neurological and/or oxidative stress.

5 Claims, 3 Drawing Sheets

8-HYDROXY-QUINOLINE DERIVATIVES

Our invention relates to novel quinoline derivatives, synthesis or these compounds, pharmaceutical compositions containing those compounds, preparation of these pharmaceutical compositions, and it relates to the use of novel 8-hydroxy-quinoline-derivatives according to the invention in the treatment and prevention of different diseases, primarily those diseases that are associated with neurological and/or oxidative stress.

Our invention discloses cytoprotective and metal chelate forcing agents and their medical use. Furthermore, the object of our invention is the treatment of ischemia, reperfusion injury, cardiovascular disorders, neurodegenerative disorders (including Alzheimer's disease and Huntington's disease) and trauma. Furthermore, the object of our invention is the treatment of depression and other neuropsychiatric disorders, including anxiety disorders. Another object of our invention is the treatment of liver, kidney or lung injuries. The compounds according to the invention can he used as neuroprotective and cardioprotective agents, and for the treatment of neuropsychiatric disorders.

Publications and cited patents referred to in the present patent specification are involved in the description as references.

The various etiological cell injuries and cell deaths are the main characteristics of many cardiovascular, neurological and inflammatory disorders. Cell injuries may occur as the results of cellular hypoxia or ischemia, formation of various kinds of oxidants or free radicals and/or overproduction of various biological mediators (cytokines, chemokines, lipid mediators). These processes are often interdependent; so those occur as parts of self-amplifying ("suicidal") intracellular cycles and form the determining basis of many human diseases. Though cell death is typically qualified as apoptosis or necrosis, these two forms only represent the two ends of the spectrum of the forms of cell injuries. The intercellular mechanisms taking part in the above cell death processes are complex, but often activate the cell death effector family called caspases and mitochondrial dysfunction, mitochondrial depolarisation, generation of reactive oxygen species and release of mitochondrial components into the cytosol (comprehensive literature; Szabó, 2005; Duprez et al., 2009; Degterev és Yuan, 2008; Wang et al., 2009). The pathway of cell death includes activation of poly(ADP-ribose) polymerase (PARP). The latter enzyme is expressed in the nuclei (comprehensive literature: Jagtap and Szabó, 2005).

The compounds preventing cell injury and cell death are usually called "cytoprotective" compounds. Cytoprotection may be achieved by many pharmacological and biochemical methods. The following examples of them are mentioned here; scavengers of oxidants and free radicals, inhibitors of certain "death effector pathways", stabilisation of cell membranes, etc. In the course of ischemia or several related disease processes, iron and copper cations are released from the tissues which catalyse hydroxy-free radical formation in the Haber-Weiss pathway in a known manner causing cell injuries. Inactivation or chelate formation of these metal cations may result in a cytoprotective affect. Thus experiments were conducted to mitigate the catalytic efficiency of iron and copper cations in such a way that iron-chelate forming siderophores (e.g. deferoxamine) were administered (Lewen et al., 2000; Britton at al., 2002).

It is known that glutamate is released along with zinc cations from the synaptosomes of the nervous system cells using glutamate as a chemical messenger. Usually, the zinc released in the nervous synapsis is quickly built again in the synaptosomes. As a result of ischemia, lasting attacks and cerebral lesion, the zinc released from the synaptosomes is accumulated in the extracellular liquid surrounding the neurons, when an excessive amount of cine enters the cell body, zinc may trigger cell death via apoptosis and necrosis. Zinc-chelate forming through that mechanism may result in neuroprotection and influence the outcome of various neuropsychiatric diseases. (Regland et al., 2001; Koh et al., 1936).

Therefore the zinc-chelating agents may also be useful in treatment of the Alzhemier's disease by binding zinc occurring in the plaques thus weakening the structure of the plagues (Frederickson et al., 2005; Schäfer et al., 2007). The zinc-chelating agents may also he useful in the treatment of Huntington's disease (Nguyen at al., 2005), According to another way of cytoprotection, the intracellular pathways mediating protective effects are induced. A prototype of this approach is the so-called "ischemic preconditioning" where the cells or organs are subjected to ischemia, for a short time in order to induce over-regulation of the cytoprotectives genes (e.g. genes of antioxidant enzymes, heat, shock proteins and others). Heme oxygenase expression of the enzyme (HO-1) has demonstrated cytoprotection in several experimental systems (e.g. Li et al., 2007; Idris et al., 2008) .

The previous patent applications relating to the cytoprotective approach pertain to the following; inhibitors of various apoptotic pathways or effectors (e.g. U.S. Pat. Nos. 6,949, 516; 6,737,511; 6,544,972; 6,521,617, 6,495,522; 7,604,389; 7,601,846; 7,533,852); maintaining the mitochondrial function during the cell injury (e.g. U.S. Pat. Nos. 6,552,076; 6,511,966; 7,550,439; 7,528,174); direct inhibition of the catalytic activity of PARP enzyme (e.g. U.S. Pat. Nos. 6,476, 048; 6,531,464; 601,719; 7,595,406; 7,550,603; 7,449,464; 7,217,709; 6,956,053; 6,534,651) over-regulation of cytoprotective genes (including heme oxygenase) (e.g. U.S. Pat. No. 7,524,819; 7,364,757).

Compounds used for inhibition of endoplasmatic reticulum stress have been described in the American patent application publication no. 2008/293699.

Cell-based screening tests have recently been performed for systematic identification of cytoprotective compounds. In this test a certain form of cell injury was simulated and a chemical library was screened in order to identify compounds preventing or retarding the cell injury. (e.g. Gero et al., 2007). The screening tests do not identify the mechanism of the effect, however, it can be identified by means of secondary tests.

By means of the cell-based screening method, we have found and identified novel hydroxy-quinoline derivatives. These compounds protect the cells from injuries induced by oxidative stress therefore these can potentially be used in the treatment of many diseases. The compounds according to the invention exert various cellular effects e.g. iron-chelating, inhibition of PARP-activation, inhibition of mitochondrial dysfunction, activation of heme oxigenase and chelate forming with iron ions. In the course of implementation of our invention the chelators are added in a form free of iron, zinc and copper cations therefore these compounds form complexes with the above cations when in contact with the physiological system.

The pharmaceutical compositions according to cur invention contain chelators as the active agent, which are not in a complex bond with iron, copper or zinc cations.

The further object of our invention is a neuroprotective and/or cardioprotective procedure for patients suffering from conditions associated with cell death. Neuroprotection and/or cardioprotection is achieved in accordance with our invention in such a way that a compound according to our invention, capable of protecting the cells from cytotoxic attacks is administered to the patient in need of treatment.

The object of our invention on the one hand is compounds with the general formula (I) and their therapeutically acceptable salts

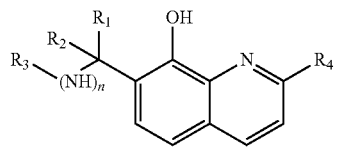

in which formula

R$_1$ represents a hydrogen atom, lower alkyl group, lower alkenyl group, lower cycloalkyl group, aryl group, aralkyl group or heterocyclic group wherein the above groups are optionally substituted with 1,2,3 or 4 electron, withdrawing groups or electron donating groups in ortho, meta and/ or para position;

R$_2$ represents a hydrogen atom, lower alkyl group, aryl group, aralkyl group, heterocyclic group wherein the above groups era optionally substituted with one or more halogen atoms;

R$_3$ represents a lower alkyl group, aryl group, aralkyl group or heterocyclic group wherein the above groups are optionally substituted with 1, 2, 3 or 4 electron withdrawing groups or electron donating groups in ortho, meta or para position;

R$_4$ represents a hydrogen atom, lower alkyl group or any acidic functional group;

n is 1 or 2,

A preferred group of the compounds with tire general formula (I) is the derivatives in which R$^1$ represents a group substituted with an electron withdrawing group in para position, or a group substituted with an electron withdrawing group in meta position, or the above group substituted with an electron donating group in ortho, meta or para position; or R$_1$ represents a group double-substituted with electron withdrawing groups in meta and para positions; or R$_1$ represents a group double-substituted with electron withdrawing groups in ortho and para position; or R$_1$ represents a substituted or unsubstituted heterocyclic group;

R$_3$ represents an aromatic group substituted with an electron withdrawing group in para position; or R$_3$ represents a heteroaromatic or alicyclic group unsubstituted or substituted with an alkyl group and/or electron withdrawing groups in ortho, meta or para position;

R$_2$ and R$_4$ represent hydrogen atom; and n is 1.

In especially preferred derivatives of the compounds of our invention with the general formula (I)

R$_1$ represents a phenyl group optionally single or double substituted with a nitro group, trifluoromethyl group, hydroxy group, fluorine atom or isopropoxy group, or pyridyl group R$_2$ represents a hydrogen atom;

R$_3$ represents a phenyl group optionally single or double substituted with a trifluoromethyl group or methoxy-carbonyl group or a pyridyl group optionally single or double substituted with a methyl group, fluorine atom, nitro group or a pyrimidyl, pyrrolidinyl, oxazolidinyl group or pyrazolyl group;

R$_4$ represents a hydrogen atom; and n is 1.

Especially preferred are the 8-hydroxy-quinoline derivatives mentioned as title compounds of the examples.

Figure 1A:
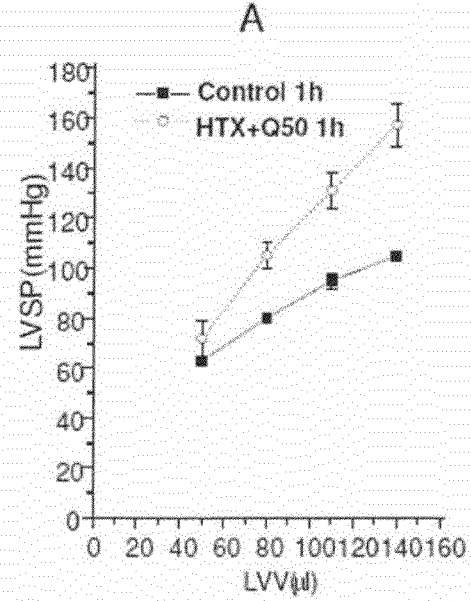
FIGS. 1a; 1b and 1c illustrate the reperfusion injury reducing effect of the compound according to Example 1 after heart transplantation.

The terms used in the description should be interpreted as follows a "lower alkyl group" means a branched or unbranched alkyl group with 1-4 carbon atoms (e.g. methyl, ethyl, isopropyl etc, group).

The term "lower alkenyl group" means a branched or unbranched alkenyl group with 2-4 carbon atoms (e.g. allyl or propenyl group).

The term "cycloalkyl group" means cyclic groups containing 3-8 carbon, atoms (e.g., cyclopropyl, cyclobutyl, cyclohexyl, etc. group).

The term "aryl group" means monocyclic or bicyclic aromatic hydrocarbon groups (e.g. phenyl, naphthyl etc. group).

The term "aralkyl group" means alkyl groups single or double substituted with above aryl groups meeting the above definition (e.g. benzyl, beta phenylethyl etc. group).

The term "heterocyclic group" means aromatic groups with 3 to 7, preferably 5 or 6 members containing one or more oxygen, nitrogen and/or sulphur atoms (e.g. pyridyl, pyrimidyl, pyrrolyl, oxazolyl etc. group).

The term "halogen atom" means bromine, fluorine, chlorine or iodine atom; fluorine and chlorine atoms are preferred.

The "electron withdrawing group" substituents are preferably halogen atoms, trifluoromethyl or nitro groups.

Of the "electron donating" substituents, the lower alkyl groups (e.g. methyl group) are mentioned.

The "acid functional group" may be any ester group (lower alkoxycarbonyl group, preferably methoxycarbonyl group) or nitrile or acid amide group.

The compounds having the general formula (I) form salts with bases on the hydroxyl groups or with acids on the nitrogen atom. For salt formation, pharmaceutically acceptable bases (e.g. alkali metal hydroxides, like e.g. sodium or potassium hydroxide) or pharmaceutically acceptable inorganic or organic acids (e.g. hydrochloric acid, hydrogen bromide, acetic acid, fumaric acid, maleic acid, malic acid, succinic acid, tartaric acid, benzene sulphonic acid, p-toluene sulphonic acid, methane sulphonic acid, etc.) can be used.

Also the object of our invention is a process for preparation of compounds with the general formula (I) and of their pharmaceutically acceptable salts, characterised in that an 8-hydroxyquinoline derivative with the general formula (II)

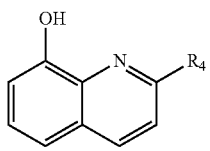

is reacted with an oxo-compound with the general formula (III)

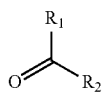

and an amine with the general formula (IV)

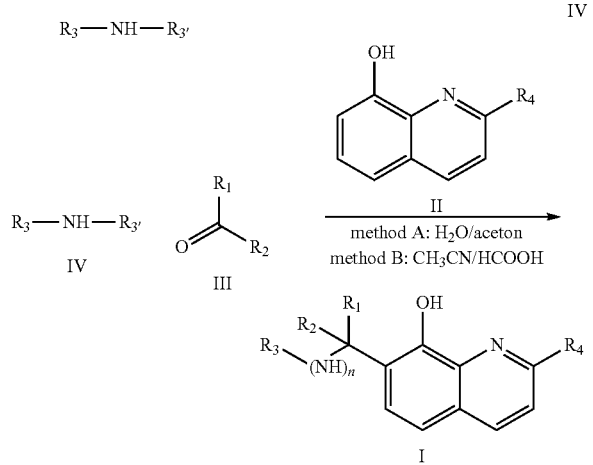

(in which formulas the substituents are as defined above and $R_3$, can be independently selected from the possible meanings of $R_3$, and $R_{3'}$ may be a hydrogen atom as well; and $R_3$ and $R_{3'}$, may be connected with as on other forming a cyclic secondary amine) then the compound with the formula (I) obtained is optionally transformed to its pharmaceutically acceptable salt or released from its salt.

The reaction is carried out using the modified Betti reaction, which is a method known (Betti, 1900; Betti, 1903; Phillips et al., 1954; Phillips et al., 1956; Phillips, 1956).

The reaction is carried out in a solvent. Water or organic solvents (e.g. acetonitrile) can be used as a reaction medium. Optionally the reaction is conducted in the presence of an acidic catalyst (e.g. formic acid).

For preparation of the compounds according to the invention—depending on the starting materials—the following method A or B were used;

Method A:

Suspend or dissolve 1 mmol of aldehyde in 2× volume, of water and add 1.1 equivalent of primary amine to the reaction mixture. Keep at 60° C. for 1 hour and, to the hot mixture, add dropwise a solution of 0.6 equivalent of 8-hydroxy-quinoline dissolved in a volume of acetonitrile or acetone which is double the volume of water. Subsequently cool the reaction mixture to room temperature and stir until precipitation occurs. Monitor the reaction by means of HPLC and TLC. Filter the precipitate, wash with acetonitrile and dry.

Method B:

Dissolve 1 mmol of aldehyde in 3× volume of acetonitrile and add 1 equivalent of amine, 0.6 equivalent of 8-hydroxy-quinoline and IV/V % formic acid to the reaction mixture. Stir the mixture until precipitation occurs or the starting quinoline spot disappears. Process the mixture by filtering, washing with acetonitrile, execute chromatography with a mixture of hexane (isomer mixture)/ethyl acetate and recrystallize from alcohol or acetonitrile.

Having completed the reaction, isolate the desired product from the reaction mixture using the usual methods (e.g. filtering or centrifuging) and purify by known methods (recrystallization or chromatography) if required.

Also the object of our invention is a pharmaceutical composition containing a compound of the general formula (I) or its pharmaceutically acceptable salt as the active agent and an inert solid or liquid pharmaceutical carrier and/or excipient.

The pharmaceutical compositions according to our invention may be solid (e.g. tablet, capsule) semi-solid (e.g. suppository) or liquid (e.g. injectable solution) preparations. The preparations can be administered orally, rectally or parenterally. The compositions according to our invention may contain common therapeutically suitable carriers and/or excipients (e.g. starch, cellulose or cellulose-derivatives, lactose, mannitol, sodium chloride, sodium carbonate, saccharose, maltose, calcium carbonate, etc.).

The pharmaceutical compositions according to our invention can be used for treatment of neurological and/or oxidative stress-related diseases during which a therapeutically efficient amount of a compound with the general formula (I) or its pharmaceutically acceptable salt is administered to the patient in need of treatment. According to a preferred embodiment of the invention the neurological or oxidative stress-related diseases are selected from the following diseases: ischemia, reperfusion injury, cardiovascular disorders, neurodegenerative disorders (including especially Alzheimer's disease and Huntington's disease), trauma, neuropsychiatric diseases (including especially depression and anxiety disorders) and liver, kidney and lung injuries.

According to the above, the pharmaceutical compositions according to our invention can be used as neuroprotective and cardioprotective agents, in the case of liver, kidney and lung injuries and for the treatment or prevention of depression, anxiety disorders, Alzheimer's disease and Huntington's disease.

Further details of our invention are described in the examples below without limiting the scope of protection to the examples.

CHEMICAL EXAMPLES

Example 1

7-((6-methylpyridin-2-ylamino) (4-nitrophenyl)methyl)quinolin-8-ol

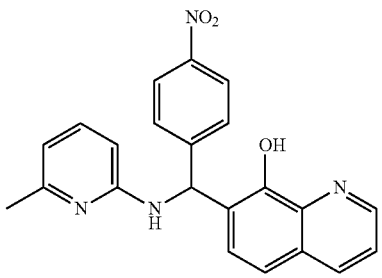 [SMILES: Cc1cccc(NC(c2ccc([N+](=O)[O-])cc2)c2ccc3cccnc3c2O)n1]

Method A:

To 10.1 g (18.5 mmol, Sigma) of 4-nitro-benzaldehyde water (20 ml) was added dropwise then 2-amino-6-picoline (7.95 g, 1.1 equivalent, Aldrich) was added to the lemon yellow suspension under intensive stirring. After a change of colour (from lemon yellow to orange yellow), a solution of 5.82 g of 8-hydroxy-quinoline (0.6 equivalent, Sigma) with 20 mL of acetone (Molar) was added to the suspension and the reaction vessel was heated at 60° C. for 4 hours then the solution was cooled to room temperature. The yellow powder precipitated was filtered (7.87 g 50.8%), washed with a small amount of acetone; its purity was checked by HPLC (≥99.5%).

Method B:

4-nitro-benzaldehyde (2.8 g, 18.5 mmol, Sigma) was dissolved in absolute acetonitrile (15 ml, Molar) and 2-amino-6-picoline (2 g, 1 equivalent, Aldrich) was added to the lemon yellow solution under stirring. 1.61 g of 8-hydroxy-quinoline (0.6 equivalent, Sigma) was added to the mixture and it was stirred at room temperature for four days. The product precipitated. (4.2 g, 27.1%) was filtered, the molecular weight of the product was verified by mass spectroscopy, its structure was demonstrated by NMR (MW: 386.1), and the purity was checked by HPLC (≥99.6%). $C_{22}H_{28}N_4O_3$ (MW: 386.1) m.p.: 157-160° C.; HPLC ($CH_3CN/H_2O$ 70:30 Phenomenex C18 282 nm): $T_r$=7.14 min $^1$H NMR 1 (DMSO) δ 2.2 (3H, s, C$\underline{H}_3$), 6.37 (1H, d, J=7.0 Hz), 6.49 (1H, d, J=7.9 Hz), 6.98 (1H, d, J=8.8 Hz, NHC$\underline{H}$), 7.28 (1H, t, J=7.9 Hz), 7.40 (2H, t, J=7.9 and 8.8 Hz), 7.50-7.55 (1H, m), 7.59-7.66 (3H, m), 8.16 (2H, d, J=8.8 Hz), 8.28 (1H, d, J=7.9 Hz), 10.1 (1H, wide s, O$\underline{H}$) $^{13}$C NMR 1 (DMSO) δ 24.2 (CH$_3$), 51.5 (CH), 105.6 (CH), 111.6 (CH), 117.17 (CH), 121.9 (CH), 123.5 (2×CH), 124.5 (Cq), 126.7 (CH), 127.7 (Cq), 128.2 (2×CH), 136.1 (CH), 137.3 (CH), 138.2 (Cq), 146.2 (Cq), 148.4 (CH), 149.8 (Cq), 152.0, 155.7 and 157.3 (Cq).

Example 2

Ethyl 4-((8-hydroxyquinolin-7-yl) (4-nitrophenyl)methylamino)benzoate

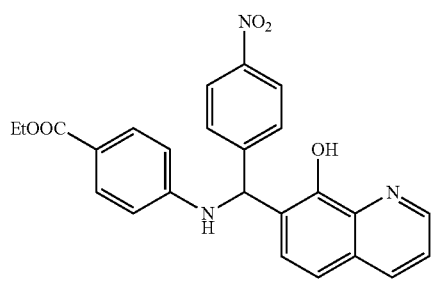 [SMILES: CCOC(=O)c1ccc(NC(c2ccc([N+](=O)[O-])cc2)c2ccc3cccnc3c2O)cc1]

The title compound was prepared by both Method A and method B presented for the compound of Example 1 with the change that benzocaine (Sigma), 4-nitro-benzaldehyde (Sigma) and 8-hydroxy quinoline were used as starting materials. Product purified by column chromatography: $C_{25}H_{21}N_3O_5$; (MW: 443.2); yield; 50 mg (30.9%, Method A). HPLC ($CH_3CN/H_2O$ 70:30 Phenomenex C-18 254 nm): $T_r$=8.82 min.

Example 3

4-{[(8-hydroxyquinolin-7-yl)-phenyl-methyl]-amino}-benzoic Acid Ethyl Ester

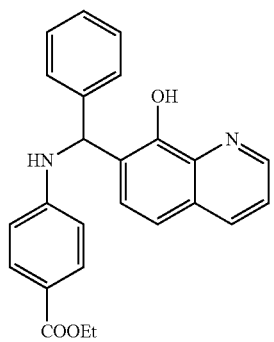 [SMILES: CCOC(=O)c1ccc(NC(c2ccccc2)c2ccc3cccnc3c2O)cc1]

$C_{25}H_{22}N_2O_3$; (MW: 398.1)
It was prepared by method A of Example 1.

Example 4

7-(phenylamino-pyridin-2-yl-methyl)-quniolin-8-ol

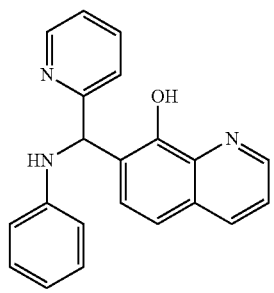 [SMILES: Oc1c(C(Nc2ccccc2)c2ccccn2)ccc2cccnc12]

$C_{21}H_{17}N_3O$; (MW: 327.1)
It was prepared by method A of Example 1.

Example 5

7-[pyridin-2-yl-(4-trifluoromethyl-phenylamino)-methyl]-quinolin-8-ol

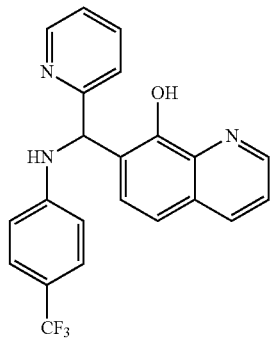 [SMILES: Oc1c(C(Nc2ccc(C(F)(F)F)cc2)c2ccccn2)ccc2cccnc12]

The title compound according to Example 5 was prepared by both, method A and method B presented for the compound of Example 1 with the change that pyridine-2-carboxaldehyde (Molar) was used as starting aldehyde and 4-trifluoromethyl-aniline (Sigma) was used as primary amine. Product purified by column chromatography: C$_{22}$H$_{16}$F$_3$N$_3$O (NW: 395.1); yield: 151 mg, (42.1%, method B); m.p.: 158-161° C.; HPLC (CH$_3$CN/H$_2$O 70:30 Phenomenex C18 254 nm): T$_r$=10.39 min. $^1$H NMR 5 (DMSO) δ 6.31 (1H, d, J=7.1 Hz), 6.79 (1H, d, J=7.6 Hz), 7.27 (1H, t, J=5.1 Hz), 7.29-7.37 (4H, m), 7.47-7.54 (3H, m), 7.75 (1H, t, J=7.2 Hz), 7.74 (1H, d, J=8.5 Hz), 8.24 (1H, d, J=8.3 Hz), 8.55 (1H, d, J=4.1 Hz), 8.85 (1H, d, J=3.2 Hz), 10.24 (1H, wide s).

Example 6

7-[(3-methyl-pyridin-2-ylamino)-(4-nitro-phenyl)-methyl]-quinolin-8-ol

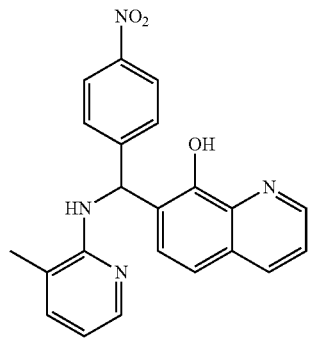 [SMILES: Cc1cccnc1NC(c1ccc([N+](=O)[O-])cc1)c1ccc2cccnc2c1O]

C$_{22}$H$_{18}$N$_4$O$_3$; (MW+1: 386.1)
It was prepared using method A of Example 1.

Example 7

7-[(6-methyl-pyridin-2-ylamino)-(4-trifluoromethyl-phenyl)-methyl]-quinolin-8-ol

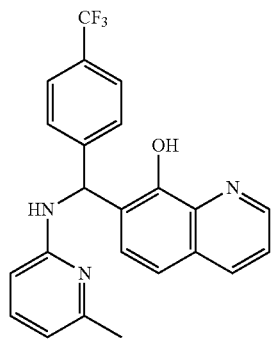 [SMILES: Cc1cccc(NC(c2ccc(C(F)(F)F)cc2)c2ccc3cccnc3c2O)n1]

The title compound was prepared by both method A and method B presented for the compound of Example 1 with the change that 4-trifluoromethyl benzaldehyde (Sigma), 2-amino-6-picoline and 8-hydroxy-quinoline were used as starting materials. Product obtained (method B): C$_{23}$H$_{18}$F$_3$N$_3$O (MW: 409.1); 229 mg, 32.5%); m.p.: 136-138° C.; HPLC (CH$_3$CN/H$_2$O 70:30 Phenomenex C18 254 nm): T$_r$=10.18 min.

Example 8

7-[(4-methyl-pyridin-2-ylamino)-(4-trifluoromethyl-phenyl)-methyl]-quinolin-8-ol

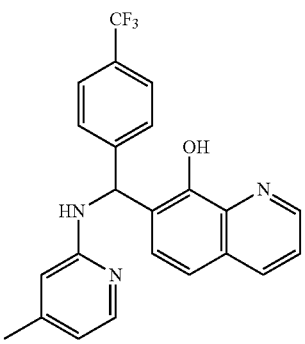 [SMILES: Cc1ccnc(NC(c2ccc(C(F)(F)F)cc2)c2ccc3cccnc3c2O)c1]

The title compound was prepared by method B presented for the compound of Example 1 with the change that 2-amino-4-methyl-pyridine (Molar), 4-trifluoromethyl-benzaldehyde (Sigma) and 8-hydroxy-quinoline (Sigma) were used as starting materials. Product obtained: C$_{23}$H$_{18}$F$_3$N$_3$O; (MW: 409.1): yield 230 mg, (29.6%) m.p.: 104-107° C.; HPLC (CH$_3$CN/H$_2$O 70:30 Phenomenex C18 282 nm): T$_r$=7.61 min. $^1$H NMR 8 (DMSO) δ 2.18 (3H, s, CH$_3$), 6.41(1H, d, J=5.1 Hz), 6.44 (1H, s, NH), 6.49 (1H, d, J=4.9 Hz), 7.07 (1H, d, J=9.2 Hz), 7.39 (1H, d, J=8.9 Hz), 7.49-7.54 (1H, m), 7.58 (2H, d, J=7.9 Hz), 7.63 (2H, d, J=8.3 Hz), 7.73 (1H, d, J=7.9 Hz), 7.85 (2H, d, J=7.9 Hz), 8.03-8.08 (1H, m), 8.12 (2H, d, J=8.5 Hz), 8.27 (1H, d, J=8.2 Hz). 8.81-8.86 (1H, m); 13C-NMR 8 (DMSO) δ 23.5 (CH3), 51.8 (NHCH), 109.5 (CH), 117.6 (CH), 121.8 (CH), 124.5 (Cq), 125.1 (CH), 125.6 2×CH), 126.8 (CH), 127.7 (2×CH), 127.8 (Cq), 130.1 (CH), 134.7 (Cq), 136.1 (CH), 138.1 (Cq), 148.2 (Cq), 148.5 (CH), 149.6 (Cq), 157.7 (CH), 161.6 (Cq), 166.3 (Cq).

Example 9

7-((4-methylpyrimidine-2-ylamino)(4-nitrophenyl)methyl)quinolin-8-ol

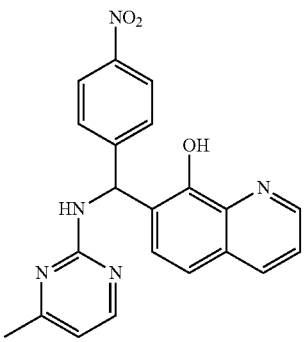 [SMILES: Cc1ccnc(NC(c2ccc([N+](=O)[O-])cc2)c2ccc3cccnc3c2O)n1]

The title compound was prepared by method B presented for the compound of Example 1 with the change that 2-amino-4-methyl-pyrimidine (Sigma), 4-nitro-benzaldehyde and 8-hydroxy-quinoline were used as starting materials. Product obtained: C$_{21}$H$_{17}$N$_5$O$_3$, (MW: 387.1); yield: 344 mg, (49.6%); m.p.: 136-145° C.; HPLC (CH$_3$CN/H$_2$O 70:30 Phenomenex C18 282 nm): T$_r$=5.21 min. NMR 9 (DMSO) δ2.14 (3H, s, CH$_3$), 6.35 (1H, d, J =5.8 Hz), 6.55 (1H, s), 7.00 (1H, d, J =8.0 Hz), 7.36-7.43(2H, m], 7.50-7.55 (1H, m), 7.56 (1H, d, J =7.5 Hz), 7.60 (1H, d, J =8.5 Hz), 7.79 (1H, d, J =5.5 Hz), 8.15 (2H, d, J =8.5 Hz), 8.28 (1H, d, J =8.5 Hz), 8.84 (s, 1H), 10.1 (s, 1H); $^{13}$C NMR 9 (DMSO) δ 20.6 (CH3), 51.6 (NHCH), 109.0 (CH), 114.2 (CH), 117.7 (CH), 121.9 (CH), 123.5 (2×CH), 124.6 (Cq), 126.7 (CH), 127.7 (Cq), 128.2 (2×CH), 136.1 (CH), 138.2 (Cq), 146.2(Cq), 147.1 (Cq), 147.2 (CH), 148.5 (CH), 149.8, 152.0 and 157.9 (3 Cq).

Example 10

7-((4-methylpyrimidin-2-ylamino) (4-(trifluoromethyl)phenyl)methyl)quinolin-8-ol

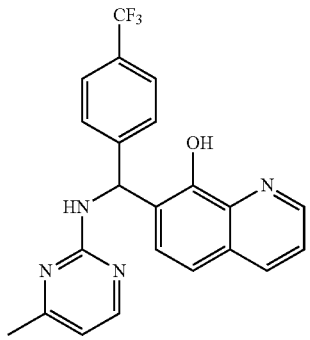 [SMILES: Cc1ccnc(NC(c2ccc(C(F)(F)F)cc2)c2ccc3cccnc3c2O)n1]

The title compound was prepared by both method A and method B presented for the compound of Example 1 with the change that 4-trifluorormethyl-benzaldehyde and 2-amino-4-methyl-pyrimidine were used as aldehyde and amine sources (Molar). Product obtained (method B), yield: 1.7 g, (34.8%); $C_{22}H_{17}F_3N_4O$; (MW: 410.1), m.p.: 144-147° C.; HPLC (CH$_3$CN/H$_2$O 70:30 Phenomenex C18 254 nm): $T_r$=7.75 min. $^1$H NMR 10 (DMSO) δ 2.24 (3H, s, CH$_3$), 6.49 (1H), d, J=5.1 Hz), 7.07 (1 H, d, J=9.0 Hz, NHC$\underline{H}$)), 7.39 (1H, d, J=8.5 Hz), 7.49-7.55 (1H, m), 7.58 (2H, d, J=7.7 Hz), 7.64 (2H, d, J=7.9 Hz), 7.74 (1H, d, J=8.5 Hz), 8.07 (1H, d, J=8.9 Hz), 8.14 (1H, d, J=4.9 Hz), 8.28 (1H, d, J=7.7 Hz), 8.83 (1H, s), 10.08 (1H, wide s).

$^{13}$C NMR 10 (DMSO) δ 23.6 (CH3), 51.7 (NHC$\underline{H}$), 110.4 (CH), 117.6 (CH), 121.8 (CH), 124.6 (Cq), 125.2 (2×CH), 126.8 (CH), 127.2 (Cq), 127.4 (Cq), 127.7 (Cq), 127.8 (2×CH), 136.1 (CH), 138.1 (Cq), 148.2 (Cq), 148.4 (CH), 149.8, 149.6, 161.6 and 167.6 (4 Cq).

Example 11

7-[(2-hydroxyphenyl)-(4-methyl-pyrimidin-2-ylamino)-methyl]-quinolin-8-ol

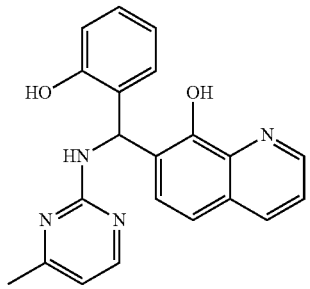 [SMILES: Cc1ccnc(NC(c2ccccc2O)c2ccc3cccnc3c2O)n1]

The title compound was prepared by method B presented for the compound of Example 1 with the change that 2-hydroxy-benzaldehyde (Molar) and 2-amino-4-methyl-pyrimidine (Sigma) were used as starting materials. The product precipitated, yield: 45 mg; $C_{21}H_{18}N_4O_2$; (MW: 358.1).

$^1$NMR 11 (DMSO) δ 2.21 (3H, s, CH$_3$), 6.39-6.46 (2H, m), 6.69 (1H, t, J=6.4 Hz), 6.75 (1H, d, J=7.7 Hz), 7.23 (1H, d, J=7.0 Hz), 7.32 (1H, d, J=8.4 Hz), 7.44-7.51 (2H, m), 7.57 (2H, d, J=8.0 Hz), 8.09 (1H, d, J=5.4 Hz), 8.25 (1H, d, J=8.0 Hz), 8.79 (1H, wide s), 9.47 (1H, wide s, O$\underline{H}$), 9.80 (1H, wide s, O$\underline{H}$).

Example 12

7-[(4-isopropoxyphenyl)-(6-methyl-pyridin-2-ylamino)-methyl]-quinolin-8-ol

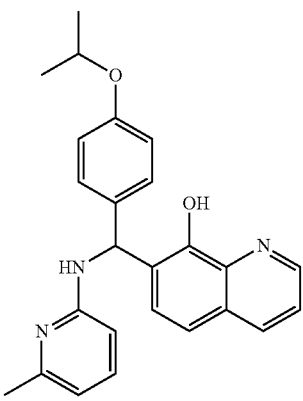 [SMILES: Cc1cccc(NC(c2ccc(OC(C)C)cc2)c2ccc3cccnc3c2O)n1]

The title compound was prepared by method B presented for the compound of Example 1 with the change that 4-isopropyl-oxy-benzaldehyde (Molar) was used as aldehyde component. Product purified by column chromatography, $C_{25}H_{25}N_3O_2$; (MW+1: 399.2), yield 135 mg, (63.1%), m.p.: 132-134° C.; HPLC (CH$_3$CN/H$_2$O 70:30 Phenomenex C18 282 nm): $T_r$=9.23 min.

Example 13

7-[(2-hydroxyphenyl)-(6-methyl-pyridin-2-ylamino)-methyl]-quinolin-8-ol

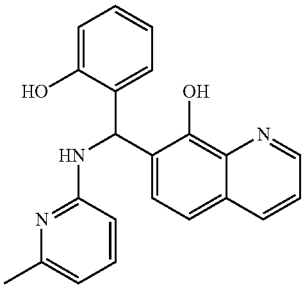 [SMILES: Cc1cccc(NC(c2ccccc2O)c2ccc3cccnc3c2O)n1]

The title compound was prepared by method B presented for the compound of Example 1 with the change that the reaction was conducted with salicylaldehyde (Molar), 2-amino-6-picoline (1 equivalent) and 8-hydroxy-quinoline (0.6 equivalent) as starting materials. Product precipitation; $C_{22}H_{19}N_3O_2$; (MW: 357.1), yield 1.6 g, (50.9%); m.p.: 189-191° C.; HPLC (CH$_3$CN/H$_2$O 70.30 Phenomenex C18 282 nm): $T_r$=5.05 min. $^1$H NMR 13 (DMSO) δ 2.23 (3H, s), 6.34 1H, d, J=6.0 Hz), 6.38 (1H, d, J=7.1 Hz), 6.69 (1H, t, J=7.2 Hz), 6.80 (2H, m) 7.02 (2H, m), 7.18 (1H, d, J=6.2 Hz), 7.25 (1H, d, J=6.8 Hz), 7.36 (1H, d, J=7.4 Hz), 7.42-7.54 (1H, m), 7.64 (1H, d, J=7.9 Hz), 8.25 (1H, d, J=7.1 Hz), 8.80 (1H, s), 9.85 (1H, s) ¯C NMR 13 (DMSO) δ 23.9 (CH3), 47.8 (CHNH), 111.1 (CH), 115.7 (CH), 116.7 (CH), 118.7 (CH), 121.5 (CH), 125.3 (Cq), 127.2 (CH), 127.4 (Cq), 127.8 (CH), 128.3 (CH), 129.2 (Cq), 135.9 (CH), 137.5 (CH), 138.2 (Cq), 148.1 (CH), 149.7, 155.1, 155.6 and 157.6 (4×Cq).

Example 14

7-[(4-fluorophenyl)-pyrrolidin-1-yl)-methyl]-quinolin-8-ol

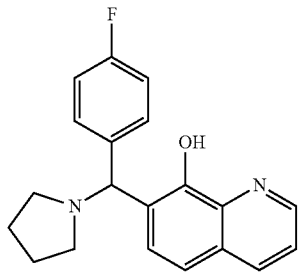 [SMILES: Oc1c(C(c2ccc(F)cc2)N2CCCC2)ccc2cccnc12]

$C_{20}H_{19}FN_2O$; (MW: 322.2)

The title compound was prepared by method A of Example 1.

Example 15

7{[(5-methyl-1,2-oxazol-3-yl)amino](3-nitrophenyl)methyl}quinolin-8-ol

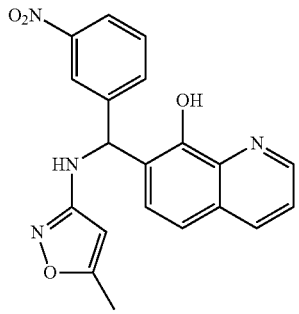 [SMILES: Cc1cc(NC(c2cccc([N+](=O)[O-])c2)c2ccc3cccnc3c2O)no1]

$C_{20}H_{16}N_4O_4$; (MW: 376.1)

The title compound was prepared by method A of Example 1.

Example 16

7-((6-methylpyridin-2-ylamino) (3,4-difluorophenyl)methyl)quinolin-8-ol

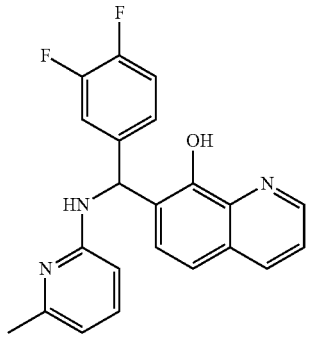 [SMILES: Cc1cccc(NC(c2ccc(F)c(F)c2)c2ccc3cccnc3c2O)n1]

The title compound was prepared by method B presented for the compound of Example 1 with the change that 3,4-difluorobenzaldehyde was reacted with 2-amino-6-picoline and 8-hydroxy-quinoline. White powder precipitated, $C_{22}H^{17}F_2N_3O$, (MW: 377.1); yield; 275 mg (53.3%). m.p.: 162-165° C.; HPLC (CH$_3$CN/H$_2$O 70:30 Phenomenex C18 282 nm): 7.97 min.

Example 17

7-((6-methylpyridin-2-ylamino) (3-(trifluoromethylphenyl)methyl)quinolin-8-ol

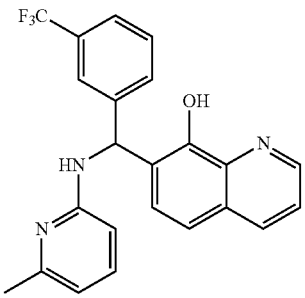 [SMILES: Cc1cccc(NC(c2cccc(C(F)(F)F)c2)c2ccc3cccnc3c2O)n1]

The title compound was prepared by method B presented for the compound of Example 1 with a higher yield. White powder precipitated, $C_{23}H_{18}F_3N_3O$ (MM: 409.1); yield: 356 mg, 57.3%. m.p.: 140-143° C., HPLC (MeOH/H$_2$O 80:20 Phenomenex C18 254 nm): 10.21 min.

Example 18

7-[(4,6-dimethyl-pyrimidin-2-ylamino)-(4-trifluoromethyl-phenyl)-methyl]-quinolin-8-ol

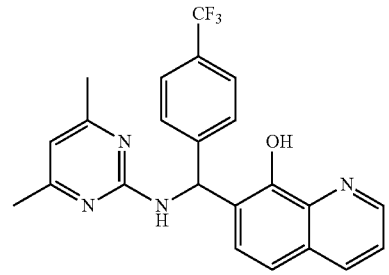 [SMILES: Cc1cc(C)nc(NC(c2ccc(C(F)(F)F)cc2)c2ccc3cccnc3c2O)n1]

The title compound was prepared by method B presented for the compound of Example 1 with a higher yield. White powder precipitated; $C_{23}H_{19}F_3N_4O$; (NW: 424.2); yield: 255 mg, (54.6%).

Example 19

7-[6-methyl-pyridin-2-ylamino)-pyridin-2-yl-methyl]-quinolin-8-ol

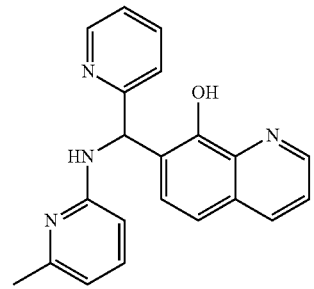 [SMILES: Cc1cccc(NC(c2ccccn2)c2ccc3cccnc3c2O)n1]

The title compound was prepared by method B presented for the compound of Example 1. Yellowish-white powder precipitated, $C_{22}H_{18}N_4O$ (MW: 342.2); yield: 1.2 g, (70.5%). m.p.: 155-157° C.

Example 20

7-[(5-fluoro-pyridin-2-ylamino)-pyridin-2-yl-methyl]-quinolin-8-ol

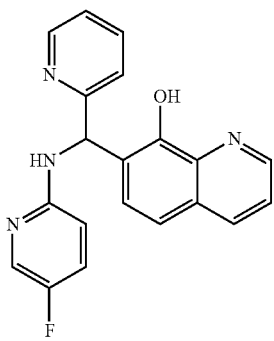

The title compound was prepared by method B presented for the compound of Example 1. Bone-coloured powder, purified by column chromatography. $C_{20}H_{15}FN_4O$; (MS: 346.1), yield 45 mg, (18.4%). m.p.: 165-168° C., HPLC ($CH_3CN/H_2O$ 70:30 Phenomenex C18 282 nm): 4.44 min.

Example 21

7-[(5-chloro-pyridin-2-ylamino)-pyridin-2-yl-methyl]-quinolin-8-ol

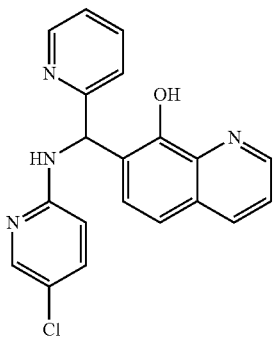 [SMILES: Oc1c(C(Nc2ccc(Cl)cn2)c2ccccn2)ccc2cccnc12]

The title compound was prepared by method B presented for the compound of Example 1; 2-amino-5-chloro-pyridine, 2-pyridine-carboxaldehyde and 8-hydroxy-quinoline were used in the reaction; the reaction mixture was heated at 60° C. for 3 days. Greyish-white powder, product purified by column chromatography. $C_{20}H_{18}ClN_4O$; (MW: 362.1); yield: 55 mg, (23.7%). m.p.: 160-162° C., HPLC ($CH_3CN/H_2O$ 70:30 Phenomenex C18 282 nm): 5.69 min.

Example 22

7-[(5-methyl-6-nitro-pyridin-2-ylamino)-(4-trifluoromethyl-phenyl)-methyl]-quinolin-8-ol

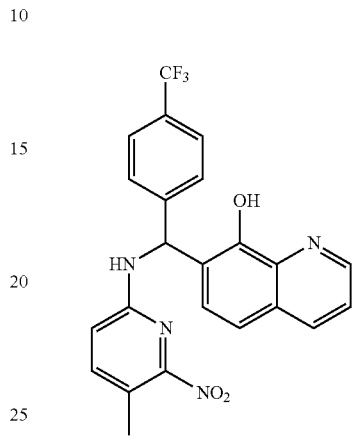

The total compound was prepared by method B presented for the compound of Example 1 with the change that 2-amino-5-methyl-6-nitro-pyridine, 4-trifluoromethyl-benzaldehyde and 8-hydroxy-quinoline were used and the reaction mixture was heated at 60° C. for 7 days.

Yellowish white powder. $C_{23}H_{17}F_3N_4O_3$; (MW: 454.1), yield: 26 mg. (10%), m.p. ≥300° C., HPLC ($CH_3CN/H_2O$ 70:30 Phenomenex C18 282 nm): $T_r$=5.60 min.

Example 23

7-[(3-hydroxy-phenyl)-(6-methyl-pyridin-2-ylamino)-methyl]-quinolin-8-ol

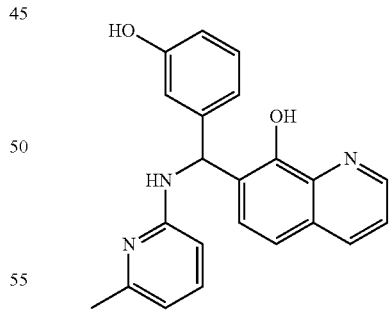

The title compound was prepared by method B presented for the compound of Example 1 with the change that 3-hydroxy-benzaldehyde was reacted with 2-methyl-6-picoline and 8-hydroxy-quinoline. White powder, purified by column chromatography. $C_{22}H_{19}N_3O_2$; (MW: 357.2), yield: 211 mg, (80.2%), m.p.: 187-189° C., HPLC ($CH_3CN/H_2O$ 70:30 Phenomenex C18 282 nm): $T_r$=3.97 min.

BIOLOGICAL EXAMPLES

Example 24

Inhibition of Activities of Matrix metalloproteinase 2 (MMP-2, 72 kDa gelatinase) and Matrix metalloproteinase 9 (MMP-9, 92 kDa gelatinase) by 7-((6-methylpyridin-2-ylamino) (4-nitrophenyl)methyl)quinolin-8-ol H9c2 rat embryonic myocardial cells (from ATCC, Rockville, Md., USA) were grown in Dulbecco's modified eagle's medium containing 10% cattle serum, 4 mM L-glutamine (Sigma-Aldrich, Hungary), 100 IU/ml penicillin and 100 ug/ml streptomycin. To the H9c2 supernatant sample, 30 uM of the compound according to Example 1 (7-((6-methylpyridin-2-ylamino (4-nitrophenyl)methyl)quinolin-8-ol from a stock solution containing 30 mM of DMSO (1000-fold dilution) was added before electrophoresis. To the control, DMSO not containing the compound according to Example 1 was added. After electrophoresis, the gel was cut in two halves following renaturation one half was incubated in such a way that 30 uM of the compound, according to Example 1 was added to it at the final concentration, while the second half (control) was incubated without it. The compound according to Example 1 completely inhibited the 72 kDa gelatinase (MMP-2) if the substance was present during incubation. It inhibited the 92 kDa gelatinase (MMP-9) as well, hut to a less extent than the 72 kDa gelatinase, MMP-9 and MMP-2 contribute to caspase-mediated endothelium cell death, after hypoxia reoxygenation via destruction of the cell-matrix interactions and the homeostatic integrin signal. The MMP-2 and MMP-9 inhibitors reduce the caspase-3 activity significantly and decrease the endothelial cell death (Lee et al., 2004).

Example 25

The compound according to Example 1 (7-((6-methylpyridin-2-ylamino) (4-nitrophenyl)methyl)quinolin-8-ol) Reduces Reperfusion Injury after Heart Transplantation A heterotropic heart transplant experiment model was performed in a way described earlier (Poly(ADP-Ribose): inhibition of polymerase reduces the reperfusion injury occurring after heart transplantation (Szabó et al. 2002) , Briefly: the donor hearts were transplanted from Lewis rats. After ischemic protection performed at 4° C. for 1 hour, the hearts were implanted intraabdominally via anastomising the aorta and the pulmonary artery of the donor heart with the abdominal aorta or vena cava of the recipient rat. Care of all animals was performed by people in line with the requirements of "Principles of Laboratory Animal Care"; National Society of Medical Research, and the Guide for the Care and Use of Laboratory Animals prepared by the National Academy of Sciences; publisher: National Institutes of Health (NIH Publication No. 86-23, revised 1996).

The functional measurements of the transplant were carried out as follows: the left ventricular systolic pressure (LVSP), left ventricular end diastolic pressure (LVEDP), rate of the change of blood pressure (dP/dt) and relaxation time constant (TE) were measured by means of a Millar micromanometer (Millar Instruments, Inc.), with different LV, using an intraventricular ballon. The total coronary blood flow (CBF) was measured on the donor aorta with perivascular ultrasonic flow sample. After determination of the baseline, the endothelium-dependent vasodilator acetylcholine (ACH, 1 nmol/l, 0.2 ml) and bradykinin (BK 0.1 nmol/l, 0.2 ml), and the endothelium-independent vasodilator sodium nitroprussid (SNP, 10 nmol/l, 0.2 ml) were added directly into the coronary arteries of the transplant through the donor aorta. Between the infusions, CBP was allowed to return to the baseline level. The vasodilator response was expressed as the maximum percentage change of CBF from the baseline.

Two transplant groups were studied (n=6/in each group). Just before loosening the aorta clamp, slow injection of common salt solution (control group) or the compound according to Example 1 (3 mg/kg) was started and it was continued during the first 5 minutes of the reperfusion period.

Measurement of the systolic and diastolic function and CBF in group A (control) and group B (compound according to Example 1) was performed 1 hour after reperfusion.

The hemodynamic parameters and myocardial blood flow were determined after 60 minute reperfusion. The heart frequency and aorta pressure of the recipient were the same in every group. The systolic functional recovery was significantly better in the group treated with the compound according to Example 1 than the control values. The LVSP and the peak positive dP/dt were significantly (P=0.05) higher in the group treated with the compound according to Example 1.

Figure 1B:
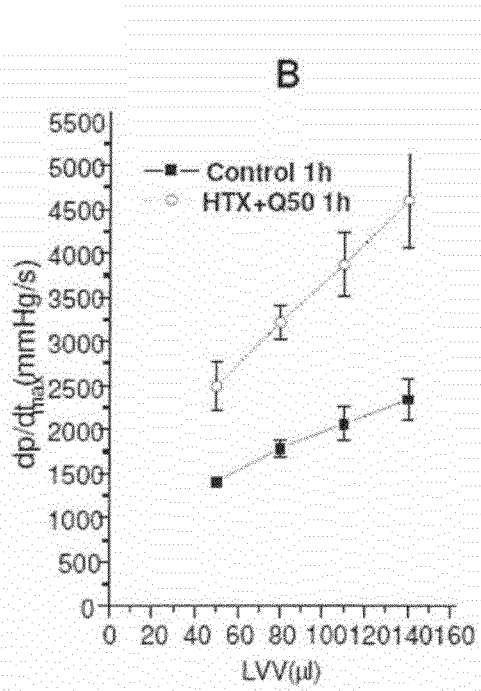
Figure 1C:
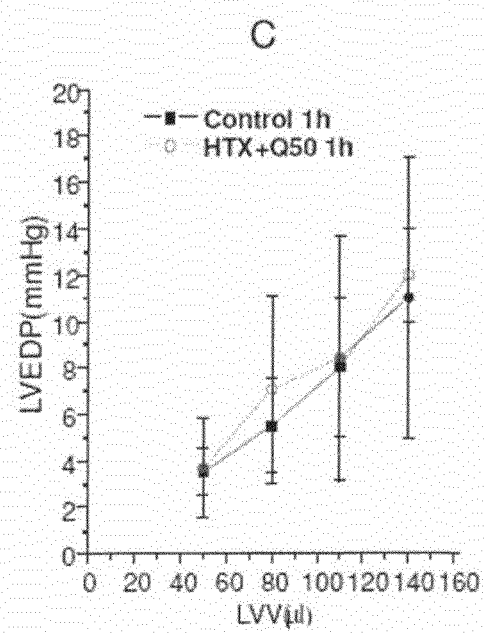

The systolic heart function curves in the group treated with the compound according to Example 1 showed a significant drift to the left compared with the group treated with the carrier (FIG. 1$a$ and FIG. 1$b$). The LVEDP did not show changing values between the groups. The diastolic cooperation curves (end diastolic pressure—volume relationship) were similar in every group (FIG. 1$c$).

Example 26

Treatment with Compounds having the General Formula (I) prevented Cell Death caused by Hydrogen Peroxide In Vitro in Heart, Neuronal and Liver Cells H9c2 rat embryonic myocardial cells (ATCC, Rockville, Md., USA) were grown in Dulbecco's modified Eagle's medium containing 10% cattle serum, 4 mM L-glutamine (Sigma-Aldrich, Hungary), 100 IU/ml penicillin and 100 ug/ml streptomycin. The cells were placed into 96-well, microtitration plates (10 000 cell/well) and after 24 hours, treated with 1% $H_2O_2$ (Sigma; solution (0.2 mM final concentration), 30 minutes after the treatment various compounds with the general formula (I) in various concentrations were put on them and after 3 and 24 hours viability of the cells was determined by means of MTT (3-(4,5-dimethyl-2-thiazolyl)-2,5-diphenyl-2H -tetrazolium bromide) test.

3-(4,5-dimethyl-2-thiazolyl)-2,5-diphenyl-2H-tetrazolium bromide (MTT, Serva) was added to the cells in 0.5 mg/ml final concentration and incubated at 37° C. for 1 hour. The cells were washed with PBS and the formazan dye was dissolved in isopropanol. The amount of the formazan dye transformed was measured by means of a Powerwave reader (Biotek, Winooski, Vt.) at 570 nm; background measurement 690 nm. The calibration curve was obtained in such a way that the capacity of the serial dilutions of the cells to transform MTT was measured and the viable cell count was calculated using Gen5 software. The measurements were executed 3 hours and 24 hours after the exposure of each series of the experiments to the effect of $H_2O_2$.

Example 27

Treatment with Various Compounds Having the General Formula (I) prevented Cell Death caused by Hydrogen Peroxide in vitro in Liver Cells Hep3B human hematoma cells (ATCC, Rockville, Md., USA) 10% were grown in Dulbecco's modified. Eagle's medium, containing 10% cattle serum, 4 mM L-glutamine (Sigma-Aldrich, Hungary), 100 IU/ml penicillin and 100 ug/ml streptomycin. The cells were kept in 100 mm TC dishes (Orange Scientific, Belgium) in an incubator in a 37° C. space containing moistened air and 5% $CO_2$.

Figure 2:
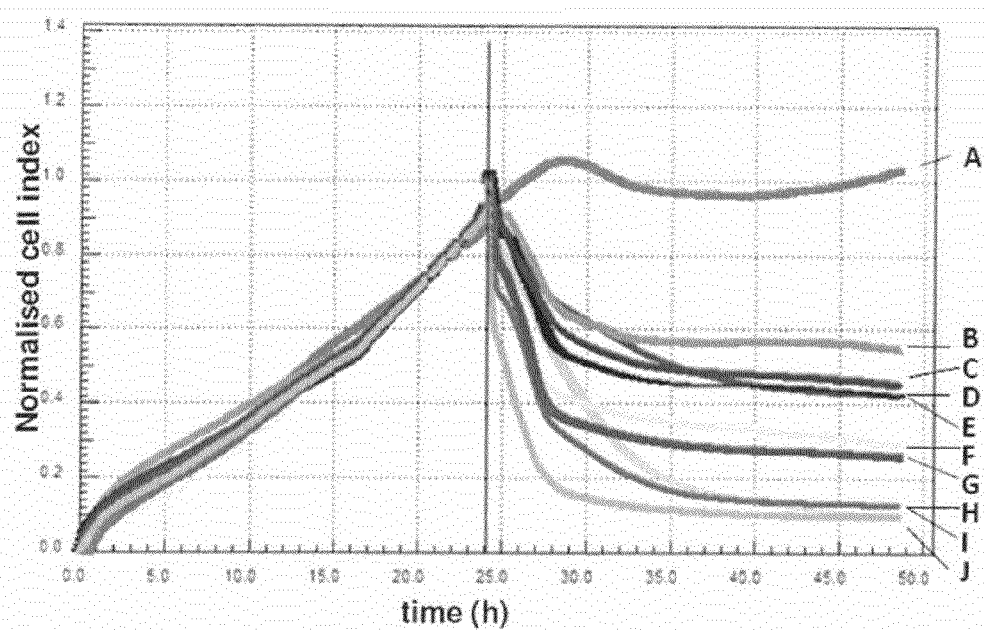
FIG. 2 illustrates the effect of several compounds according to the invention on cell death caused by hydrogen peroxide in vitro on liver cells.

The cells were placed, in 96-well E-plate (Roche) microtitration plates pre-treated with gelatine (10 000 cells/well) and grown for 16 hours. 30 minutes after the treatment, various compounds with the general formula (I) in various concentrations were put on them and the viability of the cells was measured with an Excelligence instrument by RT-CES method (Roche) continuously by determining the cell index measured in every 2 minutes. The results are shown in FIG. 2. Curve "A" represents the untreated control, curve "I" represents the compound PJ34, a known PARP inhibitor, while curve "J" represents the control treated with peroxide.

In this experiment the following compounds according to the general formula (I) were tested (indicating which curve in FIG. 2 represents the effect of the given compound on the normalized cell, index):

7-((4-nitrophenylamino) (phenyl)methyl)quinolin-8-ol (curve "B"),
4-{[(8-hydroxyquinolin-7-yl)-phenyl-methyl]-amino}-benzoic acid ethyl ester (curve "C", Example 3),
7-((4-phenylpiperazin-1-yl) (thiophen-2-yl)methyl)quinolin-8-ol (curve "D"),
7-((6-methylpyridin-2-ylamino) (4-(trifluoromethyl) phenyl) methyl) quinolin-8-ol (curve "E"),
7-((4-fluorophenyl) (thiazol-2-ylamino)methyl)quinolin-8-ol (curve "F"),
7-(phenylamino-pyridin-2-yl-methyl)-qninolin-8-ol (curve "G", Example 4) and
7-[(4-fluorophenyl)-(pyrrolidin-1-yl)-methyl]-quinolin-8-ol (curve "H", 14).

The tests were executed in order to determine the cytoprotective effect on Hep3B human hematoma cells 30 minutes after treating with $H_2O_2$. 250 uM of hydrogen peroxide was used in these cells. Cell growth is linear during the application of hydrogen peroxide. 30 minutes after the treatment with various compounds with the general formula (I) according to our invention the slopes of the cell index curves changed significantly based on which different cytoprotective effects of the compounds according to our invention can be established.

Example 28

Figure 3:
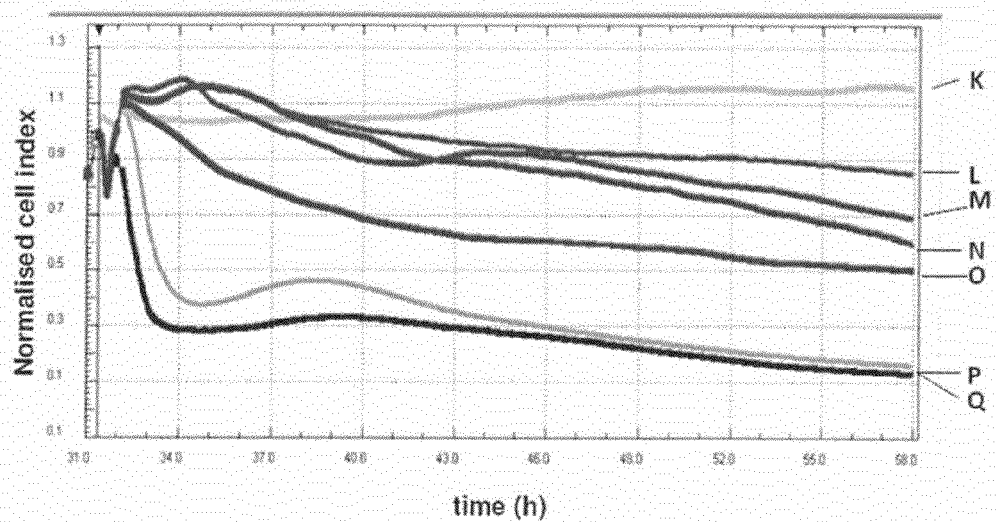
FIG. 3 illustrates the effect of several compounds according to the invention on cell death caused by hydrogen peroxide in vitro on mixed neurosis and astrocytes.

Treatment with Various Compounds having the General Formula (I) prevented Cell Death Caused by Hydrogen Peroxide in vitro on Mixed Primary Neurons and Astrocytes The cells were kept in 100 mm TC dishes (Orange Scientific, Belgium) in an incubator in a 37° C. space containing moistened air and 5% carbon dioxide. A combined culture of cerebral neurons and astrocytes was prepared following the method of Griffin S et al (Griffin et al., 2005). The cell cultures were kept in an Eagle's minimal essential medium containing 10% foetal cattle serum and 1% non-essential amino acid solution (Sigma-Aldrich, Hungary). The results are shown in FIG. 3. Curve "K" represents the untreated control, curve "P" represents the control treated with PJ34and curve "Q" represents the control treated with hydrogen peroxide.

The cells were placed in 96-well E-place (Roche) microtitration plates (10 000 cells/well) pre-treated with gelatine, and grown for 16 hours, 5 minutes before the treatment the following compounds with the general formula (I) according to our invention in 5 um concentration were put on them:

7-((6-methylpyridin-2-ylamino) (4-nitrophenyl)methyl) quinolin-8-ol (curve "L", Example 1),
7-[(6-methyl-pyridin-2-ylamino)-(4-trifluoromethyl-phenyl)-methyl]-quinolin-8-ol (curve "M", Example 7),
ethyl 4-((8-hydroxyquinolin-7-yl) (4-nitrophenyl)methylamino)benzoate (curve "N", Example 2) and
7-((4-methylpyrimidin-2-ylamino) (4-(trifluoromethyl)phenyl)methyl) quinolin-8-ol (curve "O", Example 10).

Then the viability of the cells was measured with an Excelligence instrument by RT-CES method (Roche) continuously by determining the cell index measured in every 2 minutes. The treatment started with adding 100 uM $H_2O_2$ causing destruction of 90% of the total cells in the control well not containing a compound with the general formula (I).

Example 29

Effect of the Compound according to Example 1 (7-(((6-methylpyridin-2-ylamino) (4-nitrophenyl) methyl)quinolin-8-ol) on the Behaviour of Rats Test Animals Wistar rats received from Charles River Laboratories (Budapest, Hungary) were used as test animals. App. 2 month rats were used (200-300 g body weight). The animals were conditioned for app. 1 week. The animals received standard laboratory food (Charles River Laboratories, Budapest, Hungary) and tap water ad libitum. The temperature and humidity were kept at 22±2° C. and 60±10%, respectively. The rats were kept in groups of 5 in 45×35×25 cm Makrolon cages. Day/night cycles of 12 hours were used; the light was switched off at 19:00. The experiments were conducted in the daylight period. The experiments were conducted in accordance with the European Communities Council Directive of 24 Nov. 1985 (86/609/EEC, according to the control and approval of the Animal Welfare Committee of the Institute of Experimental Medicine).

Example 29.1

Verification of Anxiety-inhibiting Effect of the Compound according to Example 1 by Elevated Plus-Maze Test Elevated Plus-maze Test A black metal box was used for the elevated plus-maze test. The sizes of the equipment axe as follows: arm length: 40 cm, arm width: 12 cm, wall height: 30 cm and platform height: 70 cm. The open arms are surrounded by 0.5 cm ledges. The test was conducted according co the following publication: Pellow et al., 1985.

In the early hours of the light phase, the rats were treated with the carrier, the compound according to Example 1 (2 mg/kg), the compound according to Example 1 (8 mg/kg) and chlordiazepoxide (8 mg/kg) (n=10 in each group). This chlordiazepoxide dose reliably reduced anxiety in this test earlier. 2 hours after the treatment the animals were placed in the centre of the equipment with their heads directed towards the closed arm. The exposure time was 5 minutes. Entries co the closed arms are indicators of locomotive activity while the use of the open arms is the indicator of the degree of anxiety. Use of the open arm was characterised by two variables: percentage share of time spent in open arms and percentage frequency of entries to open arms (100×entries to open arms/total entries to arms) (Pellow et al., 1985; Hogg, 1996).

Figure 4:
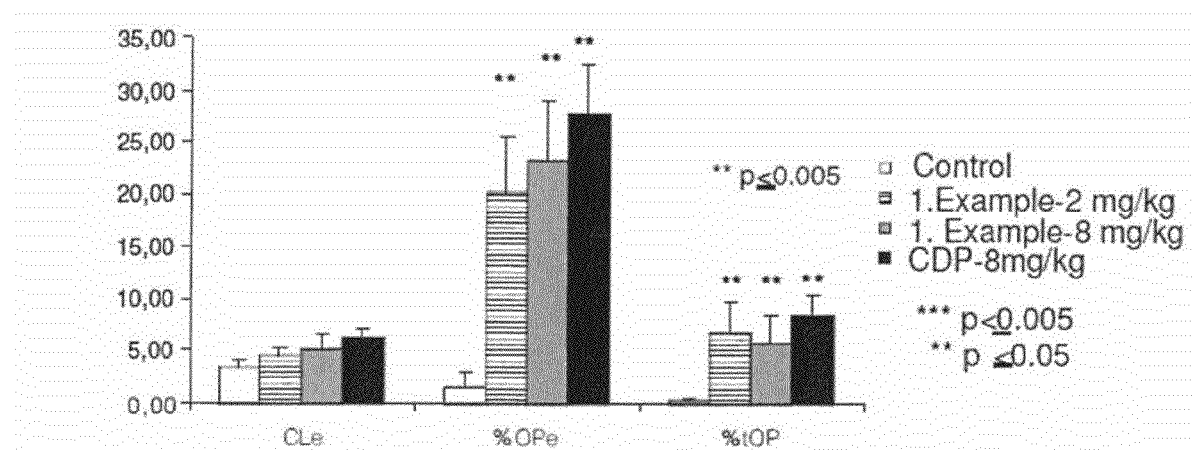
FIG. 4 illustrates the effect of the compound according to Example 1 in elevated plus-maze tests.

The results are shown in FIG. 4. In the figure, "Example 1" refers to the compound according to Example 1, CDP refers to chlordiazepoxide.

Example 29.2

Effect of the Compound according to Example 1 on Depression

Forced Swimming Test

Rats were forced to swim twice as described in the following publication: Porsolt et al., 1978. On the first day every rat was placed in a 15 cm wide, 35 cm high glass cylinder filled with water to 30 cm. At that water depth the tails of the rats did not touch the bottom of the cylinder. Water temperature was 24±0.5° C. On the following day the animals were treated with the carrier, 2 my/kg of the compound according to Example 1, 8 mg/kg of the compound according to Example 1 and 30 mg/kg imipramine. This dose of impipramine reliably reduced floating in previous experiments; in this test it is the main characteristic of depression-like behaviour. After a rest period of 2 hours the rata were forced to swim again for 5 min. Behaviour of the animals was recorded by a video camera located 2 meters from the cylinders. The following behaviour factors were recorded: struggling (the animal tries to leave the cylinder by climbing on the walls); swimming (swimming round in the cylinder) and floating (the animal makes only the movements necessary to keep its head above the wafer). The time of floating indicates the degree of depression-like behaviour in this test.

Figure 5:
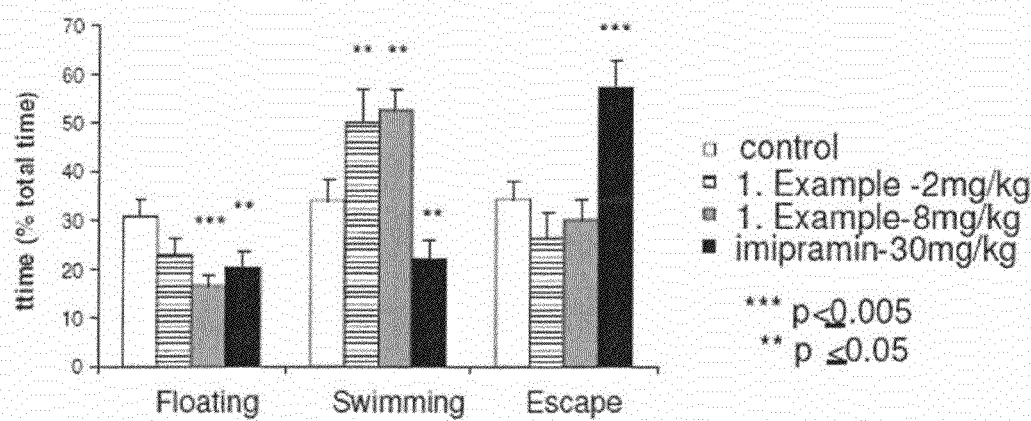
FIG. 5. illustrates the effect of the compound according to Example 1 in forced swimming tests.

The results are shown in FIG. 5. In the figure, "FIG. 1" refers to the compound according to Example 1.

Example 30

Cytotoxic Effect of the Compounds According to the Invention on Various Tumour Cell Lines In our experiment, HepG2 and Hep3B (human hepatocellular carcinoma), SUM149PT (human breast tumour), K562 (human erythroblastic leukaemia, U87 (human glioma), CCRF-CEM (human leukaemia) cell cultures were used; these were grown in the following medium: U87, CCRF-CEM; Dulbecco's Modified Eagle Medium (D-MEM) (high glucose) (Gibco BRL, Carlsbad, Calif., USA), penicillin (50 IU/ml-streptomycin (50 mg/ml), 10% foetal cattle serum.

1:1 mixture of HepG2, Hep3B, SUM149PT: Dulbecco's Modified Eagle Medium (D-MEM) (high glucose) (Gibco BRL, Carlsbad, Calif., USA) and Nutrient Mixture F-12 Ham (Sigma, St. Louis, Mo., USA), penicillin (50 IU/ml)-streptomycin (50 mg/ml), 10% foetal cattle serum.

CCRF-CEM: RPMI Media 1640 (Gibco BRL, Carlsbad, Calif., USA), penicillin (50 IU/ml-streptomycin (50 mg/ml), 10% foetal cattle serum.

The cells were placed into 96-well microtitration plates (10 000 cells/well), and after 24 hours the cells were incubated with the various substances. After incubation MTS test (3-(4, 5-dimethylthiazol-2-yl)-5-(3-carboxymethoxyphenyl)-2-(4-sulphophenyl)-2H-tetrazolium) (Promega, Madison, Wis., USA) was conducted adding it in a final concentration of 0.5 mg/ml to the cells, which were then incubated at 37° C. for 1 hour. The cells were washed with PBS and the formazan dye was dissolved in isopropanol. The amount of the formazan dye transformed was measured by means of a Powerwave reader (Biotek, Winooski, Vt.) at 570 nm; background measurement 690 nm. The calibration curve was obtained in such a way that the capacity of the serial dilutions of the cells to transform MTS was measured and the viable cell count was calculated using Gen5 software.

The results of the experiment with the various cells are shown, in Table 1. In the table the EC50 values of each substance is presented (the concentration where half of the cells died based on the results of the MTS test).

It can be seen, well that the compounds according to the present invention exhibited cytotoxic effect on. the various tumour cell lines.

TABLE 1

Cytostatic effect of various quinoline derivatives on various human tumour cell lines

| Compound's name (Example no.) | Cell line (type) | | | | | |
|---|---|---|---|---|---|---|
| | CCRF-CEM (leukaemia) | Hep3B (liver) | HepG2 (liver) | K562 (leukaemia) | SUM149PT (breast) | U87 (glioma) |
| 7-((6-methylpyridin-2-ylamino)(4-nitrophenyl)methyl)quinolin-8-ol (Example 1) | 1.0 | | 0.5 | 1.0 | 10.0 | 2.5 |
| 7-[(6-Methyl-pyridin-2-ylamino-(4-trifluoromethyl-phenyl)-methyl]-quinolin-8-ol (Example 7) | 0.3 | 5.0 | 0.5 | 15.0 | | |
| Ethyl 4-((8-hydroxyquinolin-7-yl)(4-nitrophenyl)methylamino)benzoate (Example 2) | 1.0 | 5.0 | 2.5 | | | 4.0 |

TABLE 1-continued

Cytostatic effect of various quinoline derivatives on various human tumour cell lines

| Compound's name (Example no.) | CCRF-CEM (leukaemia) | Hep3B (liver) | HepG2 (liver) | K562 (leukaemia) | SUM149PT (breast) | U87 (glioma) |
|---|---|---|---|---|---|---|
| 7-[Pyridin-2-yl-(4-trifluoromethyl-phenylamino)-methyl]-quinolin-8-ol (Example 5) | 0.1 | 2.0 | 2.0 | | | 3.5 |
| 7-((4-methylpyrimidin-2-ylamino)(4-(trifluorometh-yl)phenyl)meth-yl)quinolin-8-ol (Example 10) | | | 1.0 | 7.0 | 5.0 | 5.0 |
| 7-[(2-Hydroxyphenyl)-(4-methyl-pyrimidin-2-ylamino)-methyl]-quinolin-8-ol (Example 11) | | | 1.0 | 5.0 | | |
| 7-[(4-Methyl-pyridin-2-ylamino)-(4-trifluorometh-ylphenyl)-methyl]-quinolin-8-ol (Example 8) | | | | 8.0 | 10.0 | |
| 7-((6-methylpyridin-2-ylamino)(3,4-difluorophen-yl)methyl)quinolin-8-ol (Example 16) | | | 5.0 | 1.5 | | 2.5 |
| 7-((6-methylpyridin-2-ylamino)(2-fluoro-4-(trifluorometh-yl)phenyl)meth-yl)quinolin-8-ol | | | 1.0 | 1.5 | | 2.5 |

REFERENCES

Betti, 1900; Betti, H. Gazz. Chim. Ital. 1900, 30 II, 301;
Betti, 1903; Betti, M. Gazz. Chim, Ital. 1903, 33 II, 2;
Britton at al., 2002; Britton R S, Leicester K L, Bacon B R, Iron toxicity and chelation therapy, Int J Hematol. 2002 October; 76(3):219-228;
Duprez et al., 2009: Duprez L, Wirawan E, Vanden Berghe T, Vandenabeele P. Major cell death pathways at a glance. Microbes Infect. 2009 November;11(13):1050-1062;
Degterev és Yuan, 2008; Degterev A, Yuan J, Expansion and evolution of cell death programmes. Nat Rev Mol Cell Biol. 2008 May;9(5):378-390;
Frederickson et al., 2005: Nature Reviews Neuroscience, Vol. 6, 449-462;
Gero et al., 2007; Gerö D, Módis K, Nagy N, Szoleczky P, Tóth Z D, Dormán G, Szabó C. Oxidant-induced cardiomyocyte injury: identification of the cytoprotective effect of a dopamine 1 receptor agonist using a cell-based high-throughput assay. Int J Mol Med. 2007 November; 20(5):749-761;
Griffin et al., 2005: Griffin S, Clark J B és Canevari L: J Neurochem 95: 1015-1022, 2005,
Hogg, 19966; Hogg S. A review of the validity and variability of the elevated plus-maze as an animal model of anxiety. Pharmacol Biochem Behav. 1996 May;54 (1):21-30;
Idris et al., 2008; Idriss N K, Blann A D, Lip G Y, Hemoxyganase-1 in cardiovascular disease, J Am Coll Cardiol. 2008 Sep. 16;52(12):971-978.
Jagtap és Szabó, 2005; Jagtap P, Szabó C. Poly (ADP-ribose) polymerase and the therapeutic effects of its inhibitors, Nat Rev Drug Discov. 2005 May;4(5):421-440;
Koh et al., 1996: Koh J Y, Suh S W, Gwag B J, He Y Y, Hsu C Y, Choi D W. The role of sine in selective neuronal death after transient global cerebral ischemia, Science. 1996 May 17;272(5264):1013-1016;
Koh et al., 2001: Science, Vol. 272, 1013-1016;
Lewen et al., 2000: Lewén A, Matz P, Chan P H. Free radical pathways in CNS injury. J Neurotrauma, 2000 October;17 (10):871-890;
Lee et al., 2004; S. R. Lee, E. H. Lo: J. Cereb, Blood Flow Metab. 2004 July;24(7):720-727;

Li et al., 2007; Li C. Hossieny P, Wu B J, Qawasmeh A. Beck K, Stocker R. Pharmacologic induction of heme oxygenase-1. Antioxid Redox Signal. 2007 December; 9(12):2227-2239;

Nguyen et al., 2005: PNAS, Vol. 102(33), 11840-11845;

Pellow et al., 1985: Pellow, S., Chopin, P., File, S. E. & Briley, M. (1985) J. Neurosci. Methods, Vol. 14, 149-167;

Phillips et al., 1954: J. P. Phillips, R. W. Keown, Q. Fernando; J. Org. Chem., 1954, 19 (6), 907;

Phillips at al., 1956: J. P. Phillips, B. M. Barrall; J. Org. Chem. 1956, 21, 652;

Phillips, 1956: J. P. Phillips, Chem. Rev. 1956, 56, 286;

Porsolt et al., 1978; Porsolt R D, Anton G, Daniel M, Jalfre M (1978): Eur J Pharmacol, Vol. 47, 379-391.

Regland et al., 2001; Regland B, Lehmann W, Abedini I, Blennow K, Jonsson M, Karlsson I, Sjögren M, Wallin A, Xilinas M, Gottfries C G. Treatment of Alzheimer's disease with clioqninol. Dement Geriatr Cogn Disord. 2001 November-December;12(6):408-414;

Schäfer et al., 2007: J Mol Med, Vol. 85, 405-413;

Szabó et al, 2002: Szabó G, Bährle S, Stumpf N, Sonnenberg K, Szabó E E, Pacher P, Csont T, Schulz R, Dengler T J, Liaudet L, Jagtap P G, Southan G J, Vahl C F, Hagl S, Szabó, Circ. Res. 2002 Jan. 11;90(1):100-106;

Szabó, 2005; Szabó C. Mechanisms of cell necrosis. Crit Care Med. 2005 2005 December;33(12 Suppl):S530-534;

Wang et al., 2009; Wang Y, Dawson V L, Dawson T M, Poly(ADP-ribose) signals to mitochondrial AIF: a key event in parthanatos. Exp Neurol. 2009 August; 218(2):193-202;

The invention claimed is:

1. Compounds of the general formula (I) and their pharmaceutically acceptable salts,

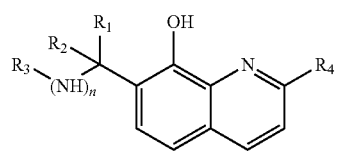

I in which formula

R$_1$ represents a phenyl group, optionally substituted in ortho, meta and/or para position with hydroxy, trifluoromethyl or nitro groups; or a pyridine group, optionally substituted in ortho, meta and/or para position with halogen atoms, hydroxy, trifluoromethyl, nitro or lower alkyl groups;

R$_2$ represents a hydrogen atom;

R$_3$ represents a pyrimidine group optionally substituted in ortho, meta or para position with halogen atoms, trifluoromethyl, nitro or lower alkyl groups;

R$_4$ represents a hydrogen atom or a methyl group;

n is 1.

2. Process for preparation of compounds with the general formula (I),

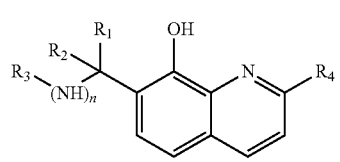

I wherein

R$_1$ represents a phenyl group optionally substituted in ortho, meta and/or para position with hydroxy, trifluoromethyl or nitro groups; or a pyridine group optionally substituted in ortho, meta and/or para position with halogen atoms, hydroxy, trifluoromethyl, nitro or lower alkyl groups;

R$_2$ represents a hydrogen atom;

R$_3$ represents a pyrimidine group optionally substituted in ortho, meta or para position with halogen atoms, trifluoromethyl, nitro or lower alkyl groups;

R$_4$ represents a hydrogen atom or a methyl group;

n is 1, characterized in that an 8-hydroxy-quinoline derivative of the general formula (II) is reacted with

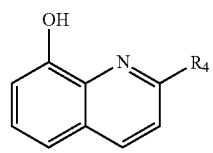

II an oxo compound of the general formula (III)

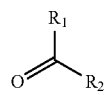

III and an amine of the general formula (IV)

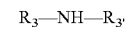

IV (wherein the substituents are as defined above, and R$_3'$ is independently selected from the meanings of R$_3$, and R$_3'$ may be a hydrogen atom as well and R$_3$ and R$_3'$ may be connected with each other forming a cyclic secondary amine) and the obtained compound of the general formula (I) is optionally transformed into a pharmaceutically acceptable acid addition salt and/or released from its salt.

3. Pharmaceutical composition containing a compound of the general formula (I) or its salt formed with a pharmaceutically acceptable acid or base and a pharmaceutically acceptable solid or liquid carrier and/or excipient.

4. Process for the preparation of the pharmaceutical compositions according to claim 3 characterized in that a compound of the general formula (I) or its pharmaceutically acceptable salt is mixed with a pharmaceutically acceptable inert solid or liquid carrier and/or excipient.

5. The compound in accordance with claim 1 which is a member of the group selected from
- 7-((4-methylpyrimidine-2-ylamino)(4-nitrophenyl)methyl)quinolin-8-ol;
- 7-((4-methylpyrimidine-2-ylamino)(4-(trifluoromethyl) phenyl) methyl)quinolin-8-ol;
- 7-[(2-hydroxyphenyl)-(4-methyl-pyrimidine-2-ylamino)-methyl]-quinolin-8-ol; and
- 7-[(4,6-dimethyl-pyrimidine-2-ylamino)-(4-trifluoromethyl-phenyl) -methyl]-quinolin-8-ol.

* * * * *

UNITED STATES PATENT AND TRADEMARK OFFICE
CERTIFICATE OF CORRECTION

PATENT NO.         : 8,871,937 B2
APPLICATION NO.    : 13/696541
DATED              : October 28, 2014
INVENTOR(S)        : Laszlo Puskas et al.

It is certified that error appears in the above-identified patent and that said Letters Patent is hereby corrected as shown below:

In the Specification

Column 1,
Line 12, "forcing" should be -- forming --.
Line 43, after "literature" delete the ";" and insert a -- : --.
Line 52, after "here" delete the ";" and insert a -- : --.

Column 2,
Line 4, "rons, when" should be -- rons. When --.
Line 4, "cine" should be -- zinc --.
Line 8, "1936" should be -- 1996 --.
Line 13, "he" should be -- be --.
Line 14, after "2005)" delete the "," and insert a -- . --.
Line 21, after "heat" delete the ",".
Line 26, after "following" delete the ";" and insert a -- : --.
Line 28, "7,604,389" should be -- 7,604,989 --.
Line 33, "601,719" should be -- 7,601,719 --.
Line 34, after "6,534,651)" insert a -- ; --.
Line 61, "cur" should be -- our --.

Column 3,
Line 26, "era" should be -- are --.
Line 36, after "2" delete the "," and insert a -- . --.
Line 37, "tire" should be -- the --.

Column 4,
Line 20, "neurosis" should be -- neurons --.
Line 26, after "follows" insert a -- : --.
Line 29, after "etc" delete the "," and insert a -- . --.

Signed and Sealed this
Nineteenth Day of May, 2015

Michelle K. Lee
*Director of the United States Patent and Trademark Office*

Line 34, after "carbon" delete the ",".

Column 5,
Line 57, after "used" delete the ";" and insert a -- : --.
Line 59, after "volume" delete the ",".

Column 7,
Line 23, after "cipitated" delete the ".".
Line 26, "$C_{22}H_{28}N_4O_3$" should be -- $C_{22}H_{18}N_4O_3$ --.
Line 65, after "yield" delete the ";" and insert a -- : --.

Column 9,
Line 2, after "both" delete the ",".
Line 8, "70.30" should be -- 70:30 --.
Line 65, "229 mg" should be -- (229 mg --.

Column 10,
Line 25, after "MW" delete the ";" and insert a -- : --.
Line 26, "409.1): yield 230" should be -- 409.1); yield: 230 --.
Line 35, "2×CH)" should be -- (2×CH) --.
Line 65, after "min." insert -- $^1$H --.

Column 12,
Line 63, "70.30" should be -- 70:30 --.

Column 13,
Line 2, "—C" should be -- $^{13}$C --.

Column 14,
Line 24, "MM:" should be -- MW: --.

Column 15,
Line 3, "$C_{22}H_{18}N_4O$" should be -- $C_{21}H_{18}N_4O$ --.
Line 67, "$C_{20}H_{18}ClN_4O$" should be -- $C_{20}H_{15}ClN_4O$" --.

Column 16,
Line 29, "total" should be -- title --.

Column 17,
Line 22, after "renaturation" insert a -- ; --.
Line 29, "hut" should be -- but --.
Line 45, after "(ADP-Ribose)" delete the ":" and insert a -- ; --.
Line 47, after "2002)", delete the "," and insert a -- . --.

Column 18,
Line 6, "CBP" should be -- CBF --.

Column 19,
Line 39, "qninolin" should be -- quinolin --.

Column 20,
Line 7, after "16 hours" delete the "," and insert a -- . --.
Line 56, "axe" should be -- are --.
Line 59, "co" should be -- to --.

Column 21,
Line 1, "co" should be -- to --.
Line 26, "my/kg" should be -- mg/kg --.
Line 31, "rata" should be -- rats --.
Line 38, "wafer" should be -- water --.

Column 22,
Line 40, after "on" delete the ".".